(12) United States Patent
Schuster et al.

(10) Patent No.: US 11,046,924 B2
(45) Date of Patent: Jun. 29, 2021

(54) SYSTEM FOR GROWING AND REPRODUCING MICROORGANISMS

(71) Applicant: Alga Pangea GmbH, Koessen (AT)

(72) Inventors: Juergen Schuster, Salzburg (AT); Ralf Ittermann, Ruhla (DE)

(73) Assignee: Alga Pangea GmbH, Koessen (AT)

( * ) Notice: Subject to any disclaimer, the term of this patent is extended or adjusted under 35 U.S.C. 154(b) by 450 days.

(21) Appl. No.: 15/984,770

(22) Filed: May 21, 2018

(65) Prior Publication Data

US 2018/0265830 A1 Sep. 20, 2018

Related U.S. Application Data

(63) Continuation of application No. PCT/EP2016/077983, filed on Nov. 17, 2016.

(30) Foreign Application Priority Data

Nov. 20, 2015 (DE) ...................... 10 2015 222 932.7

(51) Int. Cl.
*C12M 1/02* (2006.01)
*C12M 1/38* (2006.01)
*C12M 1/00* (2006.01)

(52) U.S. Cl.
CPC ............ *C12M 21/02* (2013.01); *C12M 1/02* (2013.01); *C12M 1/38* (2013.01); *C12M 23/18* (2013.01); *C12M 23/34* (2013.01); *C12M 27/20* (2013.01); *C12M 31/08* (2013.01); *C12M 31/10* (2013.01); *C12M 41/22* (2013.01)

(58) Field of Classification Search
None
See application file for complete search history.

(56) References Cited

U.S. PATENT DOCUMENTS

| 7,374,928 B2 | 5/2008 | Trösch |
| 2011/0078949 A1 | 4/2011 | Schuster et al. |
| 2012/0122224 A1 | 5/2012 | Schael et al. |
| 2012/0270304 A1* | 10/2012 | Johnson ................. C12M 41/32 435/257.1 |

(Continued)

FOREIGN PATENT DOCUMENTS

| DE | 4134813 A1 | 4/1993 |
| DE | 4411486 C1 | 3/1995 |

(Continued)

OTHER PUBLICATIONS

International Search Report dated Feb. 2, 2017 in corresponding application PCT/EP2016/077983.

(Continued)

*Primary Examiner* — William H. Beisner
(74) *Attorney, Agent, or Firm* — Muncy, Geissler, Olds & Lowe, P.C.

(57) ABSTRACT

A system for growing and reproducing microorganisms that includes a basin system that includes a number of basins, where each basin has a vertical meandering system which is formed by partitions and which can be illuminated, each basin is filled with a nutrient suspension, at least one outer wall of each basin is double-walled such that a cavity is formed, a temperature control medium for controlling the temperature of the nutrient suspension can flow through the cavity.

10 Claims, 4 Drawing Sheets

(56) References Cited

U.S. PATENT DOCUMENTS

2013/0078708 A1* 3/2013 Roux Dit Buisson ........................ C12M 41/12
435/257.1

FOREIGN PATENT DOCUMENTS

| DE | 102008026829 A1 | 12/2009 |
| DE | 102009021059 A1 | 8/2010 |
| DE | 102009020527 A1 | 11/2010 |
| DE | 102010060420 A1 | 5/2012 |
| DE | 102013109747 A1 | 3/2015 |
| DE | 102013114925 A1 * | 7/2015 ............ C12M 41/48 |
| EP | 1326959 A1 | 7/2003 |
| EP | 2584030 A1 | 4/2013 |

OTHER PUBLICATIONS

Neubauer, "Industrial Utilization of Photosynthesis", Hessen Bio-tech News, Hessian Ministry of Economics, Energy, Transport and Regional Development.

Kaldenhoff, "Microalgae Factory of the Future", Hoch3Forschen, Technische Universitaet Hamburg.

* cited by examiner

SYSTEM FOR GROWING AND REPRODUCING MICROORGANISMS

This nonprovisional application is a continuation of International Application No. PCT/EP2016/077983, which was filed on Nov. 17, 2016, and which claims priority to German Patent Application No. DE 10 2015 222 932.7, which was filed in Germany on Nov. 20, 2015, and which are both herein incorporated by reference.

BACKGROUND OF THE INVENTION

Field of the Invention

The present invention relates to a system for growing and reproducing microorganisms.

Description of the Background Art

The growth and reproduction of microorganisms, such as algae, using basin systems is known. Such basin systems have, for example, a vertical meandering system formed by partitions, wherein a nutrient suspension is introduced into the basin system and flows through it.

One factor that significantly influences the growth of microorganisms is the temperature of the nutrient suspension. The temperature causes a base activation of biological systems in the cells of the microorganisms, including in particular the absorption of carbon dioxide, photons and nutrients in the form of organic fertilizer materials. Once an ideal temperature of the nutrient suspension is reached, the biological systems mentioned can be optimized. The ideal temperature and a tolerance range deviating from the ideal temperature vary depending on the type of microorganism.

The temperature of the nutrient suspension is substantially affected by heat generation in the production of artificial light for illuminating the nutrient suspension as well as heat development during photosynthesis in the cells of the microorganisms. As a result, the real temperature can greatly deviate from the ideal temperature, creating a climate in the basin system which is no longer optimal for the growing of microorganisms.

DE 10 2008 026 829 A1, which corresponds to US 2011/0078949, discloses a system for growing and reproducing microorganisms in which light is introduced in a nutrient suspension. Further, DE 41 34 813 A1 discloses a unit for the cultivation of phototropic microorganisms. DE 10 2013 109 747 A1 discloses an apparatus for the production of phytoplankton.

SUMMARY OF THE INVENTION

It is therefore an object of the present invention to provide an improved system over the prior art for growing and reproducing microorganisms.

A system according to the invention for growing and reproducing microorganisms having a basin system comprises a number of basins, wherein in each case a basin has an illuminable vertical meandering system formed by a partition. In each case, a basin is filled with a nutrient suspension. At least one outer wall of each basin is double-walled to form a cavity, wherein the cavity can be flowed through by a temperature control medium to control the temperature of the nutrient suspension.

The thus constructed system ensures optimum temperature control of the nutrient suspension. Due to the fact that the nutrient suspension is in constant contact with the outer walls, a close thermal coupling between the temperature control medium and the nutrient suspension is achieved. This considerably improves the growing and reproducing of microorganisms over the prior art.

The outer walls can be double-walled over their entire flat side, so that homogeneous temperature control of the nutrient suspension is possible. For example, as a temperature control medium, a liquid such as water or liquid hydrogen is used.

The outer walls can each include a thermally conductive material, e.g., stainless steel. The outer walls can thus be directly thermally coupled with the nutrient suspension and transmit the heat of the nutrient suspension to the temperature control medium.

At least one temperature detection unit for detecting a temperature within a basin can be provided.

For example, the at least one temperature detection unit can be provided for detecting the temperature of the nutrient suspension, wherein the at least one temperature detection unit may be disposed on an inner wall side of an outer wall of a basin. In this case, the temperature of the nutrient suspension is directly measured, wherein preferably each basin comprises a certain number of temperature detection units.

Additionally or optionally, the at least one temperature detection unit for detecting a temperature of the temperature control medium is provided. For this purpose, the temperature detection unit is disposed on an outer wall side of the outer wall, the inner wall side of the outer wall, or in the temperature control medium itself.

In addition, the at least one temperature detection unit is provided in addition to or optionally for detecting the temperature of a contact surface coupled with a lighting unit, so that the waste heat generated by the lighting unit can be measured. The lighting unit comprises, for example, a light emitting diode arrangement, which is arranged in the partition walls. In this case, the at least one temperature detection unit is disposed, for example, on a partition wall.

A control circuit can be provided, which is fed the temperature of the temperature control medium detected by the at least one temperature detection unit as an input variable.

The control circuit comprises a control unit which regulates the temperature of the temperature control medium as a function of the temperature detected by the at least one temperature detection unit.

Furthermore, the control circuit can include a data processing unit for the analysis of the temperature detected by the at least one temperature detection unit. To this end, the data processing unit can be coupled to the control unit. As an input variable, the data processing unit receives the temperature detected by the at least one temperature detection unit and stores it, where applicable, as temperature data. Here, the control circuit is designed as a digital control circuit. Alternatively, the control circuit may also be constructed as an analog control circuit, without a data processing unit.

In addition, the control circuit comprises an actuator for setting a temperature of the temperature control medium predetermined by the control unit. The actuator can be, for example, a temperature control element or a separate temperature control circuit.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

For better illustration, a three-dimensional coordinate system having an x-axis, a y-axis and a z-axis is shown in all FIGS. 1 to 6. The z-axis is a vertical axis and the x-axis and y-axis are a horizontal axis, respectively.

Figure 1:
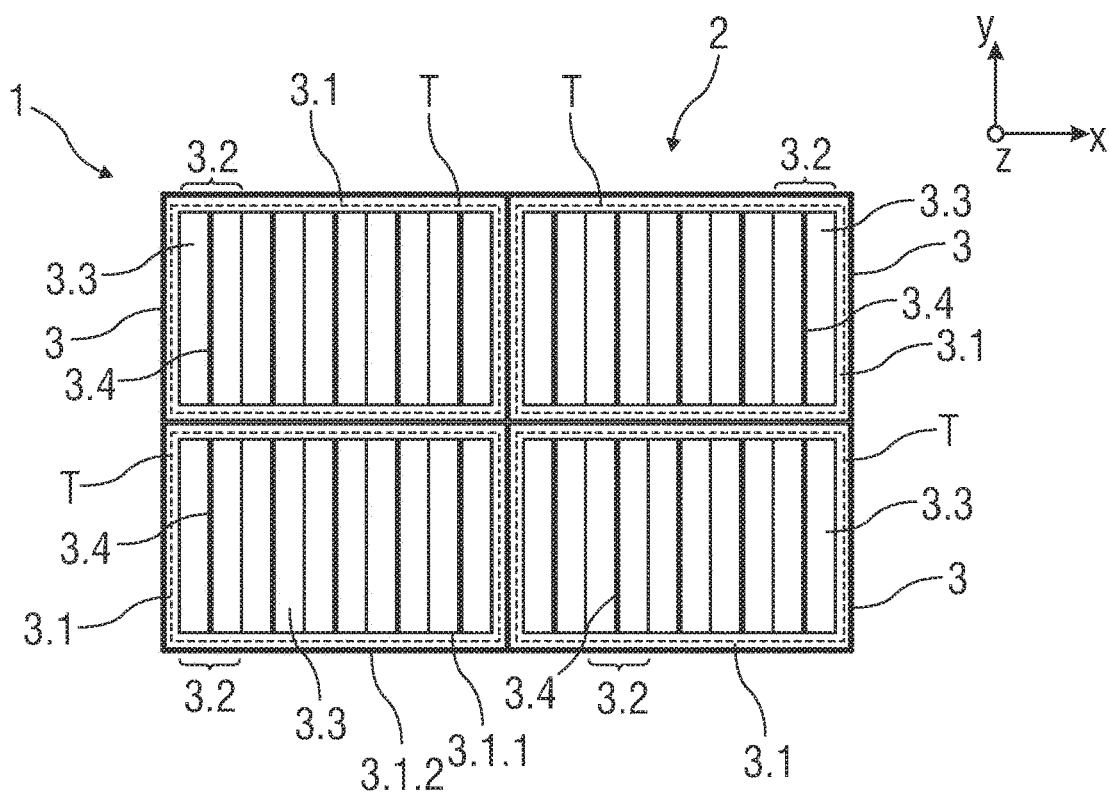
FIG. 1 is a schematic plan view of an embodiment of a system for growing and reproducing microorganisms having four basins.

FIG. 1 shows a schematic plan view of an exemplar embodiment of a system 1 according to the invention for growing and reproducing microorganisms, such as algae.

Figure 3:
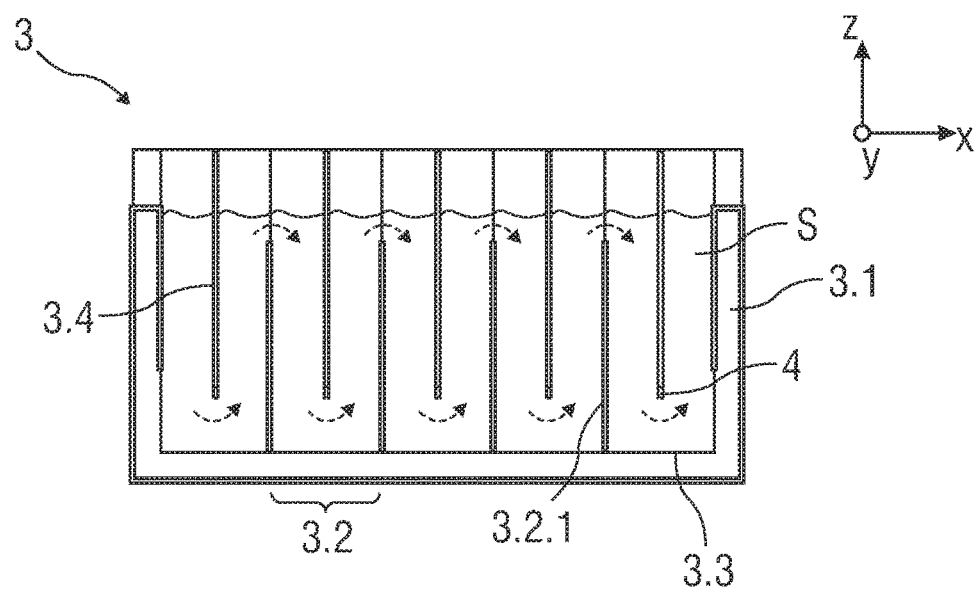
FIG. 3 is a schematic sectional view of an embodiment of a basin.
Figure 4:
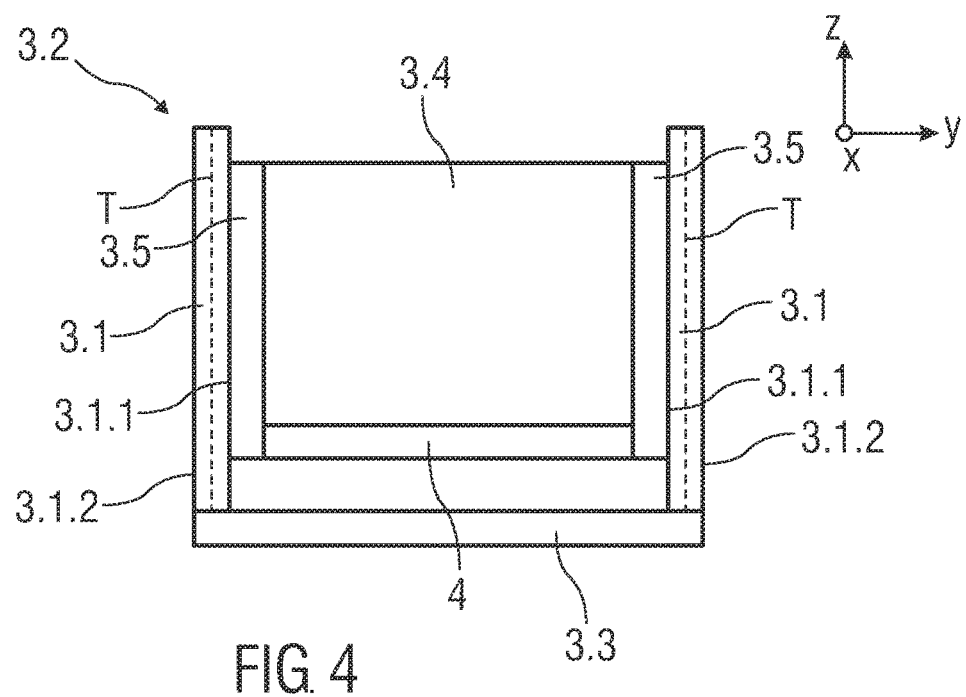
FIG. 4 is a schematic side view of a section of a basin.

The system 1 comprises a basin system 2 with exemplary four basins 3 and a nutrient suspension S disposed in the basin system 2, which is shown in FIGS. 3 and 4.

The basins 3 are formed in a modular manner and each have outer walls 3.1, which define an interior of the basins 3 for receiving the nutrient suspension S. Within the basins 3, in each case individual basin cells 3.2 adjacently disposed in the direction of the x-axis are arranged with a substantially U-shaped cross-section, which are designed to be open towards the top in the direction of the z-axis.

Each basin cell 3.2 is defined in the direction of the x-axis by two side walls 3.2.1, which extend in the direction of the y-axis in each case within the basin 3 between two outer walls 3.1, thereby protruding from a basin bottom 3.3 upwards in the direction of the z-axis. The side walls 3.2.1 of adjacent basin cells 3.2 are dimensioned such that an overflow area of the nutrient suspension S is formed from one basin cell 3.2 into the adjacent basin cell 3.2.

Furthermore, a partition 3.4 arranged between the side walls 3.2.1 and running parallel to these is immersed in each of the basin cells 3.2. The partitions 3.4 are spaced in each case from the basin bottom 3.3 in the direction of the z-axis. This way, a vertical meandering system 3.4 is formed in each basin 3 by a partition, wherein a substantially vertically directed flow of the nutrient suspension S can be achieved in the basin system 2.

The nutrient suspension S can be introduced in the basin system 2 by means of a pump or a movable plate, thereby generating a flow, which however is not further discussed in detail in the context of this application.

Figure 2:
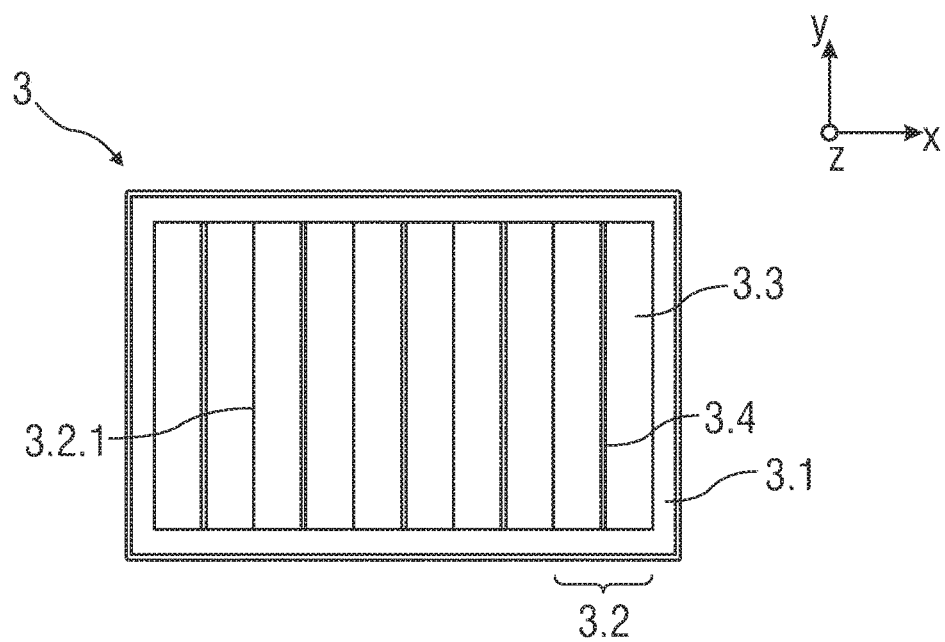
FIG. 2 is a schematic plan view of an embodiment of a basin.

FIGS. 2 and 3 show a basin 3 in several views, wherein FIG. 2 shows the basin 3 in a plan view, and FIG. 3 shows the basin 3 in a sectional view, in particular, in a longitudinal section.

Within a basin 3, the nutrient suspension S follows a substantially vertical flow in the region between a side wall 3.2.1 and a partition 3.4. In the overflow areas, and in the area between the basin bottom 3.3 and an end of the partition 3.4 facing the basin bottom 3.3, the flow is deflected, as shown by arrows in FIG. 3, such that the vertical meandering system is formed.

The partitions 3.4 are immersed in the respective basin cells 3.2 as centrally as possible, so that the distances between the partition 3.4 and the respective adjacent side walls in the direction of the x-axis are the same. For securing the partitions 3.4, for example, these can be connected with the outer walls 3.1 in a force-locking or a form-fitting manner, or in a combination of both a force-locking and form-fitting manner, by means of supports 3.5 exemplified in FIG. 4.

Figure 5:
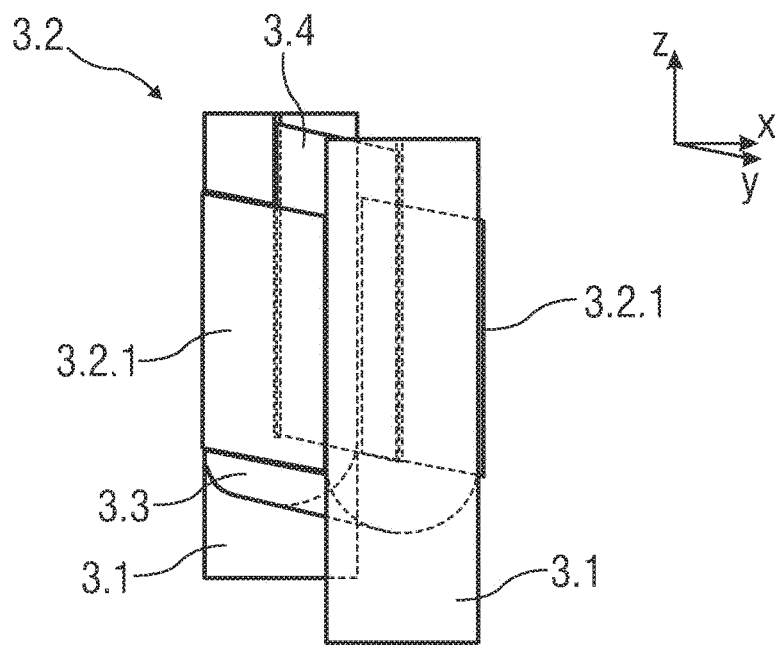
FIG. 5 is a schematic perspective view of a section of a basin.
Figure 6:
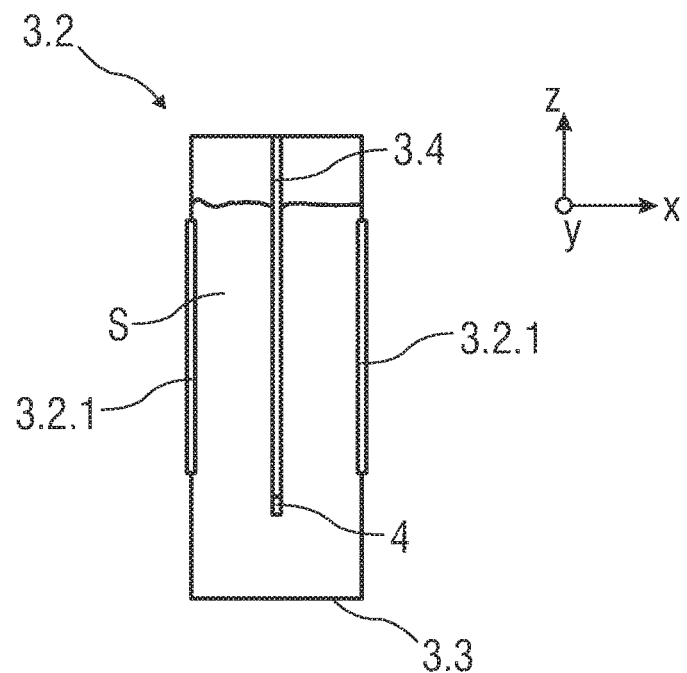
FIG. 6 is a schematic sectional view of a section of a basin.

To better illustrate the fixing of the partitions 3.4, FIG. 4 shows a side view of a section of a basin 3. FIGS. 5 and 6 each show a single basin cell 3.2, wherein FIG. 5 shows the basin cell 3.2 in a perspective view and FIG. 6 shows it in a side view.

The supports 3.5 run in the direction of the z-axis, parallel to the outer walls 3.1, and have, for example, guide slots which form-fittingly receive the edges of the partitions 3.4 so that these can be inserted into the respective basin cells 3.2.

Furthermore, a lighting unit 4 is shown, which is provided for introducing light and heat into the nutrient suspension S. The lighting unit 4 is disposed at a lower end of the partition 3.4, as seen in the viewing direction, and comprises a number of light sources, e.g., light emitting diodes or light bulbs or other suitable lighting elements.

The light generated by the lighting unit 4 is delivered to the nutrient suspension S via translucent areas in the partition 3.4. The translucent areas can be formed over the entire circumferential surface of the partitions 3.4, wherein the partition 3.4 is entirely or partially formed of frosted glass or a transparent plastic.

In addition, the nutrient suspension S can be illuminated by sunlight.

As already described above, in addition to the lighting, the temperature of the nutrient suspension S is an essential influencing factor on the growing of microorganisms.

The temperature of the nutrient suspension S is influenced on the one hand by heat produced during the lighting of the nutrient suspension S, in particular waste heat of the light-ing-emitting elements, and on the other hand by heat produced during photosynthesis in the cells of the microorganisms.

Since a maximum growth and cell division process is desirable in the growing of microorganisms, the light input is intensified for the lighting. However, greater heat generation also results from a greater lighting intensity, because due to the spatially close arrangement of the lighting unit 4 to the nutrient suspension S, higher waste heat of the light-emitting elements also causes further heating of the nutrient suspension S. This can lead to an undesired deviation of the temperature of the nutrient suspension S from an ideal value or a tolerance range.

As part of the invention, therefore, for optimum temperature control of the nutrient suspension S, the outer walls 3.1. of the basins 3 are double-walled. In this case, the outer walls 3.1 can be partially double-walled, or individual outer walls 3.1 or all outer walls 3.1 may be double-walled. It is also conceivable to design the side walls 3.2.1 and the basin bottom 3.3 double-walled.

The outer walls 3.1 of a basin 3 thus have an inner wall side 3.1.1 and an outer wall side 3.1.2, between which a cavity is formed which can be flowed through by a temperature control medium T.

The temperature control medium T is preferably a liquid, e.g., liquid sodium, liquid hydrogen, a saline solution or the like, and flows through the double-walled outer wall 3.1 in the direction of the x-axis, y-axis and/or z-axis. It is also conceivable to arrange channel structures for guiding the flow in the cavity that is formed between the outer wall side 3.1.2 and inner wall side 3.1.1.

Preferably, the outer walls 3.1 are each made of a material with high heat conductivity, e.g., stainless steel, so that an ideal heat transfer between the outer walls 3.1 and the temperature control medium T as well as between the outer walls 3.1 and the nutrient suspension S and other elements contacting the outer wall 3.1 is possible.

Due to the outer walls 3.1 being in constant contact with the nutrient suspension S, a close thermal coupling between the temperature control medium T and the nutrient suspension S is possible. Via the supports 3.5, a close thermal coupling between the temperature control medium T and the lighting unit 4 is also established, so that waste heat from the lighting unit 4 can be conducted away by means of the temperature control medium T.

The cavities of adjacent outer walls 3.1 can thereby be fluidically connected or form in each case a separate cavity, which can be connected to a temperature control line extending beyond the basin system 2.

Figure 7:
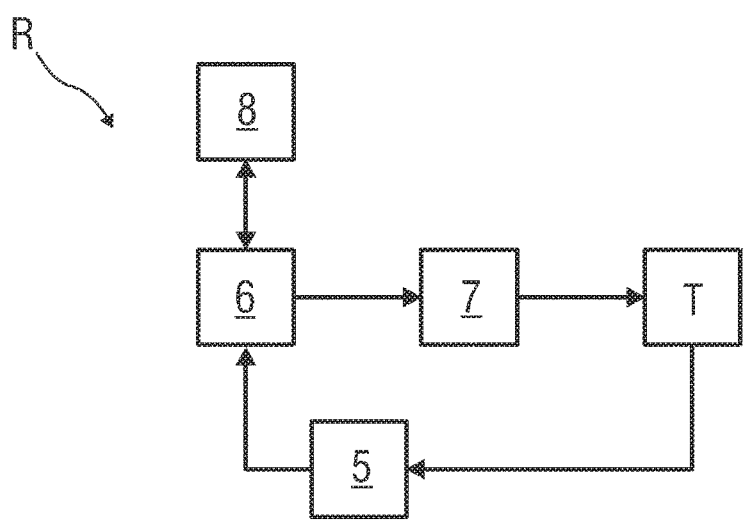
FIG. 7 is a schematic block diagram of a control circuit of the system.

For regulating the temperature of the temperature control medium T, a digital control circuit R schematically illustrated in FIG. 7 is provided.

As variables to be controlled, the control circuit R comprises a temperature of the temperature control medium T, at least one temperature detection unit 5 for indirectly or directly detecting the actual temperature of the temperature control medium T, and a control unit 6 for regulating the actual temperature control medium to a target temperature, and an actuator 7, which adjusts the target temperature predetermined by the control unit 6.

The at least one temperature detection unit 5 is provided for detecting the temperature of the temperature control medium T, which is arranged at the outer wall side 3.1.2 or the inner wall side 3.1.1 of the outer wall 3.1, or in the temperature control medium T itself. The at least one temperature detection unit 5 is formed as a well-known temperature sensor.

Alternatively, the at least one temperature detection unit 5 may be provided for detecting a temperature of the nutrient suspension S, wherein the at least one temperature detection unit 5 is disposed on the inner wall side 3.1.1 of the outer wall 3.1. The temperature of the nutrient suspension S is in this case directly detected, each basin 3 preferably comprising a certain number of temperature detection units 5.

Furthermore, additionally or optionally at least one temperature detection unit 5 can be provided for detecting the temperature of a contact surface coupled to the lighting unit 4, so that waste heat generated by the lighting unit 4 can be detected. In this case, the at least one temperature detection unit 5 is arranged, for example, on a partition wall 3.4.

Furthermore, it is possible that a plurality of temperature detection units 5 are disposed at various locations in the basin 3, especially at the aforementioned locations in the basin 3, so that a plurality of temperature data is acquired.

The temperature data collected is used as an input variable for the control unit 6, which compares said data to a target variable and accordingly, conveys a control variable to the actuator 7, e.g., a heat exchanger. Thus, as a function of even a plurality of input variables, the temperature of the temperature control medium T can be controlled.

For analyzing the input variables in the control unit 6, this is coupled with a data processing unit 8. Alternatively, the data processing unit 8 is integrated into the control unit 6. If necessary, the data processing unit 8 stores the input variables as temperature data.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A system for growing and reproducing microorganisms, the system having a basin system comprising at least two basins,
wherein the at least two basins have an illuminable vertical meandering system formed by partitions, the illuminable vertical meandering system comprising at least one light unit,
wherein a nutrient suspension is introduced in each basin of the at least two basins,
wherein at least one outer wall of the at least two basins are formed double-walled to form a cavity,
wherein the cavity is adapted to be flowed through by a temperature control medium for controlling a temperature of the nutrient suspension
wherein the at least one outer wall is connected to the at least one light unit via supports, and
wherein a thermal coupling between the temperature control medium and the at least one light unit is established via the supports for conducting away a waste heat from the light unit.

2. The system according to claim 1, wherein the at least one outer wall comprises a thermally conductive material.

3. The system according to claim 1, further comprising at least one temperature detector unit that detects a temperature within a respective basin of the at least two basins.

4. The system according to claim 3, wherein the at least one temperature detector unit detects a temperature of the nutrient suspension.

5. The system according to claim 3, wherein the at least one temperature detector unit detects a temperature of the temperature control medium.

6. The system according to claim 1, wherein the at least one temperature detector unit detects a temperature of a contact surface that is coupled with the at least one light unit.

7. The system according to claim 1, further comprising a control circuit that receives a temperature of the temperature control medium detected by at least one temperature detector unit as an input variable.

8. The system according to claim 7, wherein the control circuit comprises a controller unit that regulates the temperature of the temperature control medium as a function of the temperature detected by the at least one temperature detector unit.

9. The system according to claim 8, wherein the control circuit comprises a data processor unit to analyze the temperature detected by the at least one temperature detector unit, and wherein the data processor unit is coupled with the controller unit.

10. The system according to claim 8, wherein the control circuit comprises an actuator for setting the temperature of the temperature control medium that is predetermined by the controller unit.

* * * * *